(12) United States Patent
Karvandi

(10) Patent No.: US 12,090,078 B1
(45) Date of Patent: Sep. 17, 2024

(54) ADJUSTABLE TOE SEPARATOR DEVICE AND METHOD OF IMPROVING FOOT FUNCTIONING

(71) Applicant: Kusha Karvandi, Scottsdale, AZ (US)

(72) Inventor: Kusha Karvandi, Scottsdale, AZ (US)

( * ) Notice: Subject to any disclaimer, the term of this patent is extended or adjusted under 35 U.S.C. 154(b) by 0 days.

(21) Appl. No.: 18/501,486

(22) Filed: Nov. 3, 2023

(51) Int. Cl.
*A61F 5/01* (2006.01)

(52) U.S. Cl.
CPC .................................. *A61F 5/019* (2013.01)

(58) Field of Classification Search
CPC .......... A61F 5/01; A61F 5/019; A61F 5/0127; A61F 5/14; A61F 13/06; A61F 13/068; A61F 5/0585; A43B 7/26; A43B 7/1415; A63B 23/16
USPC ........................................................... 602/30
See application file for complete search history.

(56) References Cited

U.S. PATENT DOCUMENTS

| 1,080,303 A | | 12/1913 | Scholl | |
|---|---|---|---|---|
| 1,080,304 A | | 12/1913 | Scholl | |
| 1,080,305 A | * | 12/1913 | Scholl | A61F 5/019 |
| | | | | 602/30 |
| 2005/0251081 | A1* | 11/2005 | McClanahan | A61F 5/10 |
| | | | | 602/30 |

* cited by examiner

*Primary Examiner* — Alireza Nia
*Assistant Examiner* — Daniel A Miller
(74) *Attorney, Agent, or Firm* — Dunlap Bennett & Ludwig, PLLC

(57) ABSTRACT

A toe separator system for improving foot functionality. The toe separator system provides a toe separator shell circumscribing a plurality of toe wedges spaced apart to define a plurality of toe slots. Each toe wedge may have a pill-receiving interior volume for removably receiving a separator pill of different shapes, sizes and densities so that a user can selectively increase the resulting width and form factor of each toe wedge based on the comfort level and desired foot functioning improvement a wearer desires.

9 Claims, 5 Drawing Sheets

ADJUSTABLE TOE SEPARATOR DEVICE AND METHOD OF IMPROVING FOOT FUNCTIONING

BACKGROUND OF THE INVENTION

The present invention relates to toe separators and, more particularly, to an adjustable toe separator device.

Healthy feet are widest at the toes. However, conventional shoes, which most people have been wearing since childhood, feature a narrow toe box (the part of the shoes where your toes sit). A lifetime of squishing feet into narrow shoes causes the actual shape of the feet to change, and so causing dysfunction in foot mechanics, mobility, posture, and physical fitness. Specifically, when toes point inwards, the connective tissue of our feet shortens, circulation is restricted, and the formation of bunions is not uncommon.

Reclaiming foot health involves, among other things, wearing toe separators to assist the foot in returning to its natural shape, again, widest at the toes since the long-term benefits of toe spacing includes increased circulation, improved balance, and stronger feet.

However, just as one shoe does not fit every foot, no single toe separator fits every set of toes. Current toe separator devices are not adjustable and do not have pull tabs to make it easier to put the device on, which is a common challenge with this type of snugly fit device.

In short, many users of current toe separators find that they do not work well because the user often finds the device to either be too hard, too soft, too big, too small, too tight, or too loose.

As can be seen, there is a need for an adjustable toe separator device and a related method for improving foot functionality.

SUMMARY OF THE INVENTION

The present invention helps train the toes to spread wider to restore the natural shape and mechanics of the foot.

The present invention utilizes a swappable toe separator pill dimensioned and adapted to be inserted into one of each toe wedge, thereby selectively widening the width of each toe wedge. Each toe separator wedge may be a substantially U-shaped wedge, whereby the separator pill can be urged into an opening of the toe separator wedge to customize user comfort, experience, and individual needs. The toe separator pills come in different densities to provide an even further level of customization for the user. Additionally, the toe separator shell has pull tabs to make it easier to pull and position the device on the toes correctly.

The present invention provides a completely customizable fit and separation of the toes for the user to address their individual needs and preferences.

In one aspect of the present invention, a toe separator system, the system includes the following: a toe separator shell comprising a plurality of toe wedges, wherein space between two adjacent toe wedges defines a toe slot; each toe wedge defines a pill-receiving volume and an opening that communicates an external environment with the pill-receiving volume; and a plurality of separator pills dimensioned and shaped to be removably received in the pill-receiving volume via its opening in a nested condition.

In another aspect of the present invention, the toe separator system further includes the following: wherein at least one separator pill has an oval plane section, wherein no more than five percent of the oval plane section protrudes from the pill-receiving volume in the nested condition, wherein at least one separator pill has a fish shape having a caudal fin portion, wherein the caudal fin portion substantially protrudes from the opening in the nested condition, wherein the opening is posteriorly facing or wherein the opening is anteriorly facing, wherein each toe wedge has elastic properties for snugly accommodating one of the plurality of separator pills, wherein the toe separator shell has a pull tab disposed on each lateral end, and wherein the plurality of separator pills have a plurality of densities, respectively.

In another aspect of the present invention, a method of improving foot functionality includes the following: providing the above-mentioned toe separator system; urging a separator pill into each pill-receiving volume, respectively; sliding the toe separator shell over a set of toes of a patient; and swapping out a separator pill of at least one pill-receiving volume based on feedback from the patient.

These and other features, aspects and advantages of the present invention will become better understood with reference to the following drawings, description and claims.

DETAILED DESCRIPTION OF THE INVENTION

Figure 1:
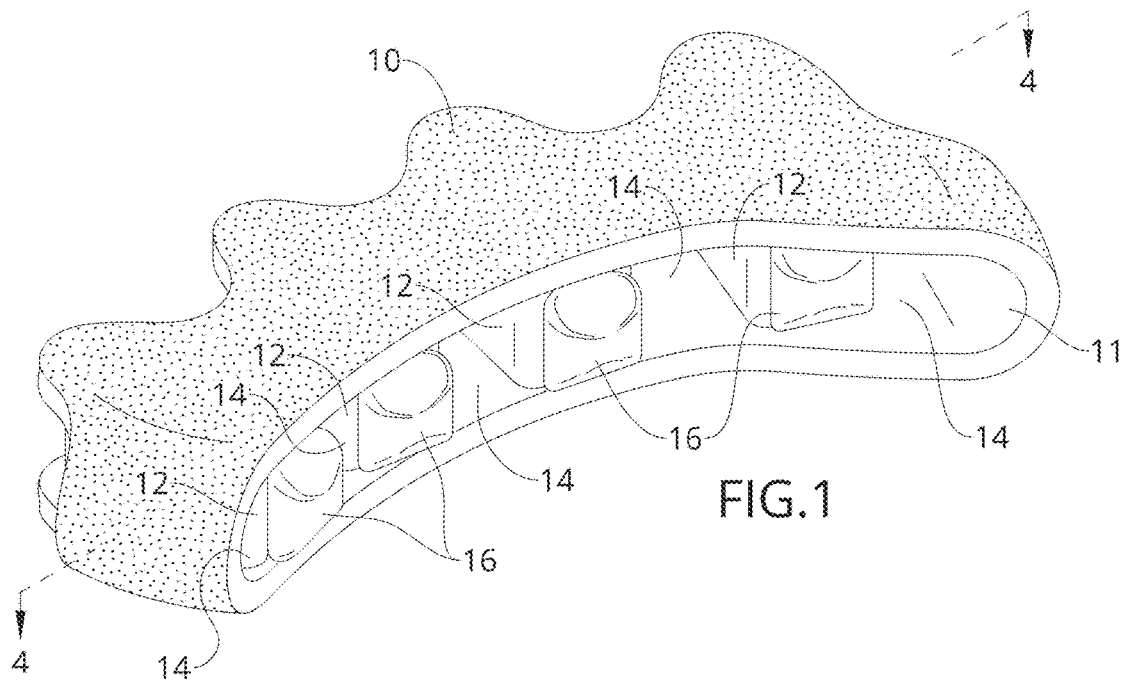
FIG. 1 is a perspective view of an exemplary embodiment of the present invention, showing the separator pills in a nested condition.
Figure 2:
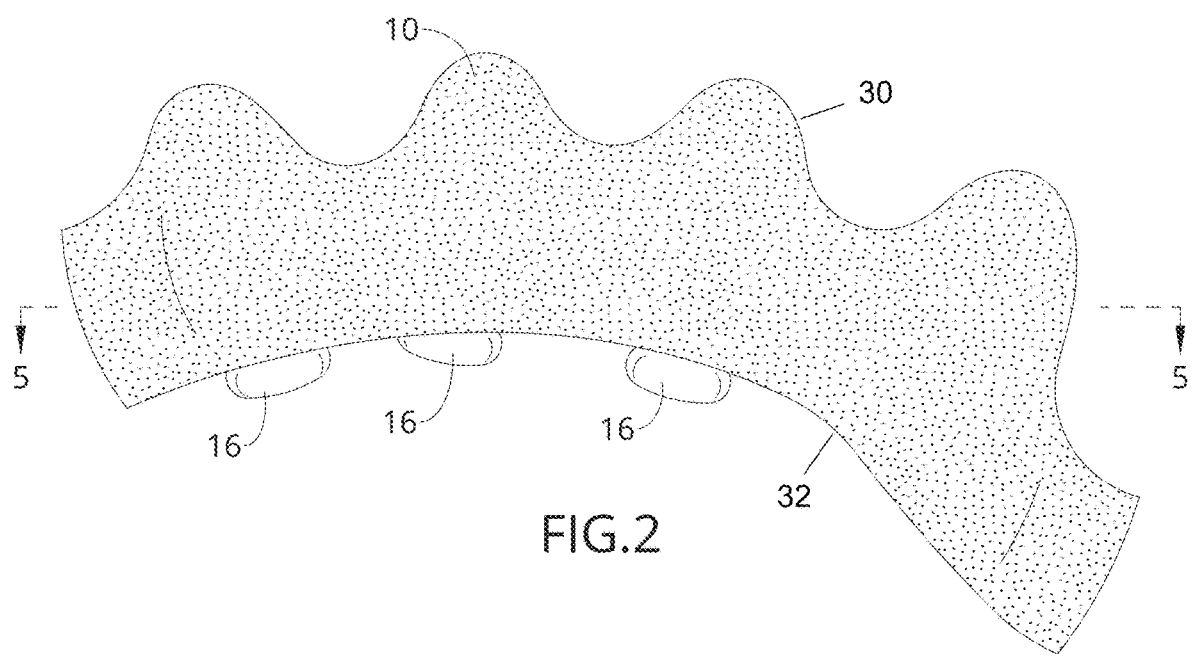
FIG. 2 is a top plan view of an exemplary embodiment of the present invention, illustrating a leading edge 30 of a toe separator shell and a trailing edge 32 of the toe separator shell, wherein the leading edge 30 is configured to be adjacent a distal end of a user's toes, and wherein the trailing edge 32 is configured to be adjacent a proximal end of the user's toes.
Figure 3:
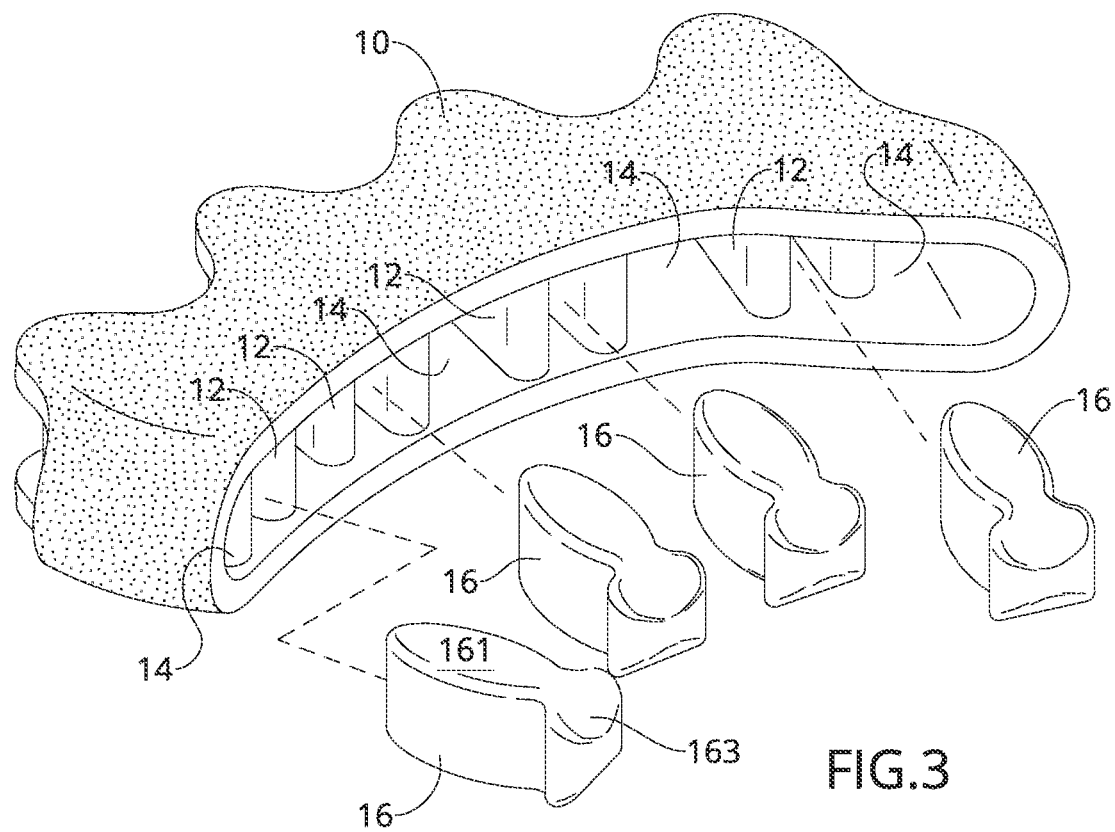
FIG. 3 is an exploded perspective view of an exemplary embodiment of the present invention.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Referring to FIGS. 1 through 9, the present invention provides a toe separator shell 10 having an upper wall, bottom wall and two sidewalls that define a shell opening 11, through which a user may insert their toes 20. The texture along the outer and inner surface of the toe separator shell 10 (the texture can be seen as stippling in FIG. 1) provides added grip to make it easier to put the toe separator on the foot. Upon doing so, the interdigital spaces between adjacent toes 20 engage a toe wedge 12. Two adjacent toe wedges 12 define a toe slot 14 therebetween. Thus, in embodiments where there are four spaced apart toe wedges 12, there would be five toe slots 14; it being understood that the present invention may be embodied in a toe separator shell 10 having one to four toe wedges 12.

Figure 4:
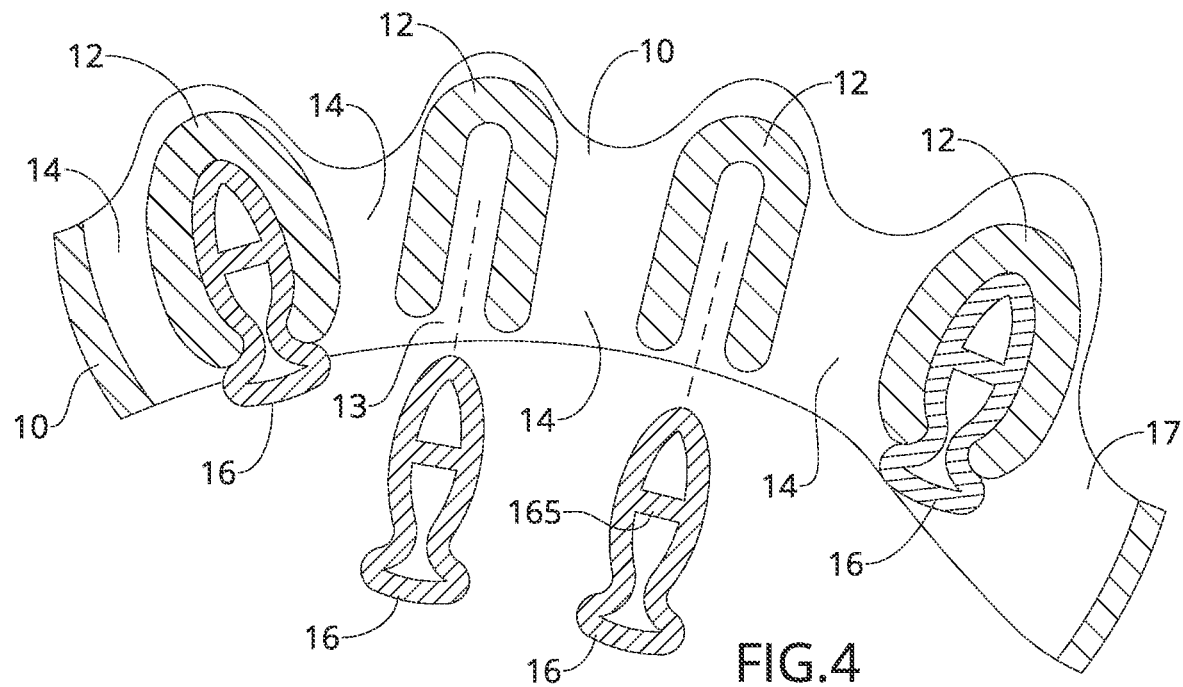
FIG. 4 is a section view of an exemplary embodiment of the present invention, taken along line 4-4 in FIG. 1.
Figure 5:
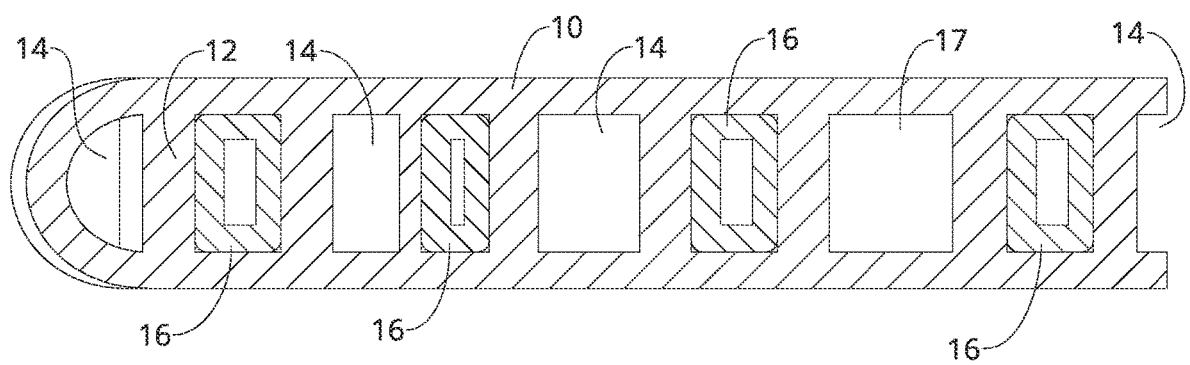
FIG. 5 is a section view of an exemplary embodiment of the present invention, taken along line 5-5 in FIG. 2.
Figure 6:
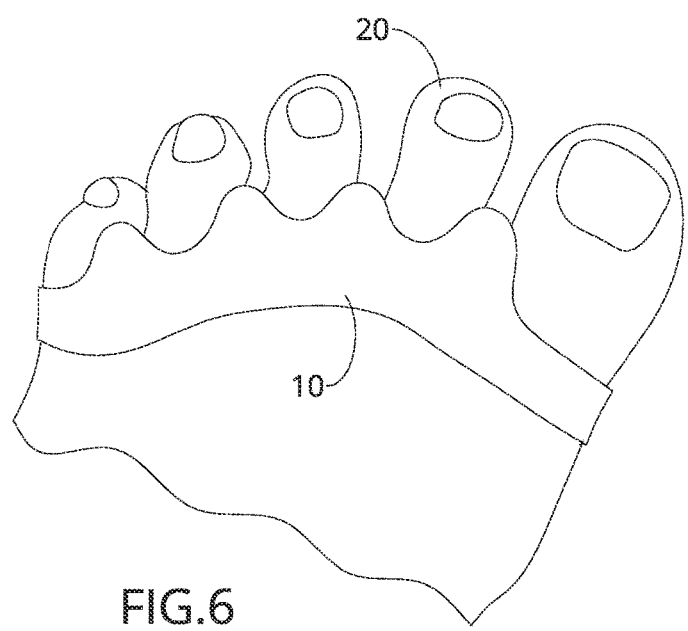
FIG. 6 is a top plan view of an exemplary embodiment of the present invention, shown in use.
Figure 7:
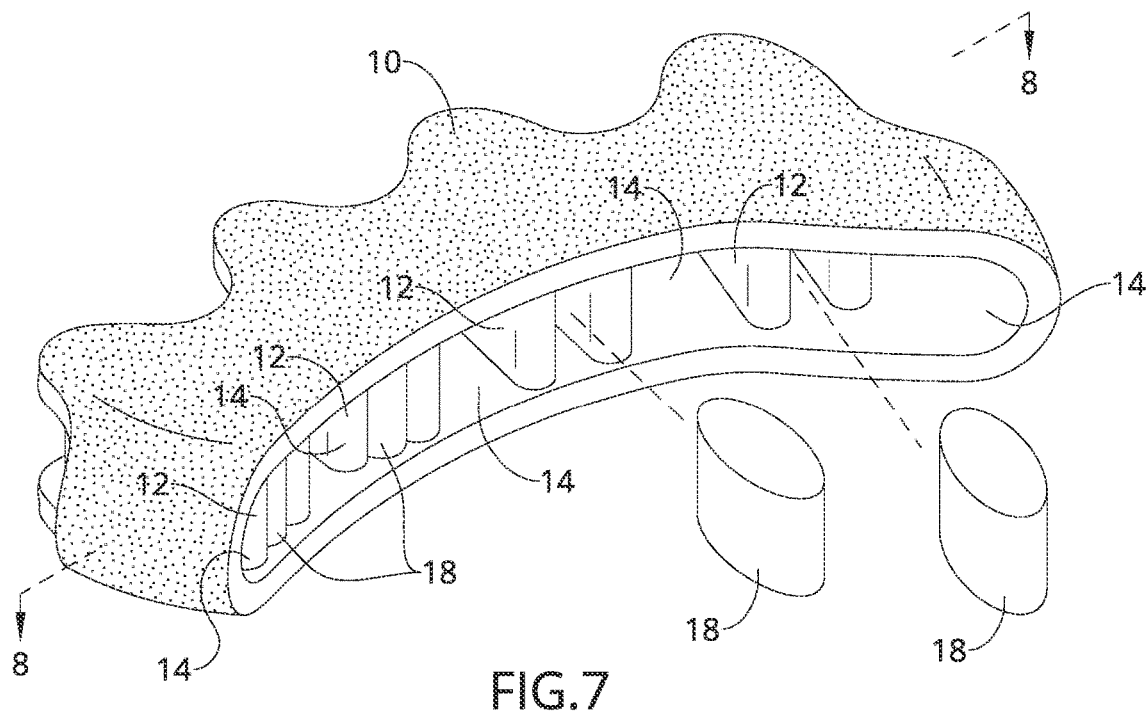
FIG. 7 is an exploded perspective view of an exemplary embodiment of the present invention.

Each toe wedge 12 may be substantially U-shaped with an opening 13 to the U-shape wedge 12 being posterior facing, as illustrated in FIG. 4 in view of FIG. 6 (though in some embodiments the opening 13 may be anteriorly facing for removably swapping out various separator pills 16, 18, 19, etc., while the present invention is being worn). Note, the toe wedge 12 need not be U-shaped, as long as it affords a pill-receiving interior volume for removably receiving a separator pill of different shapes, sizes and densities so that a user can selectively increase the resulting width and form factor of each toe wedge based on the comfort level and desired foot functioning improvement a wearer desires.

Figure 8:
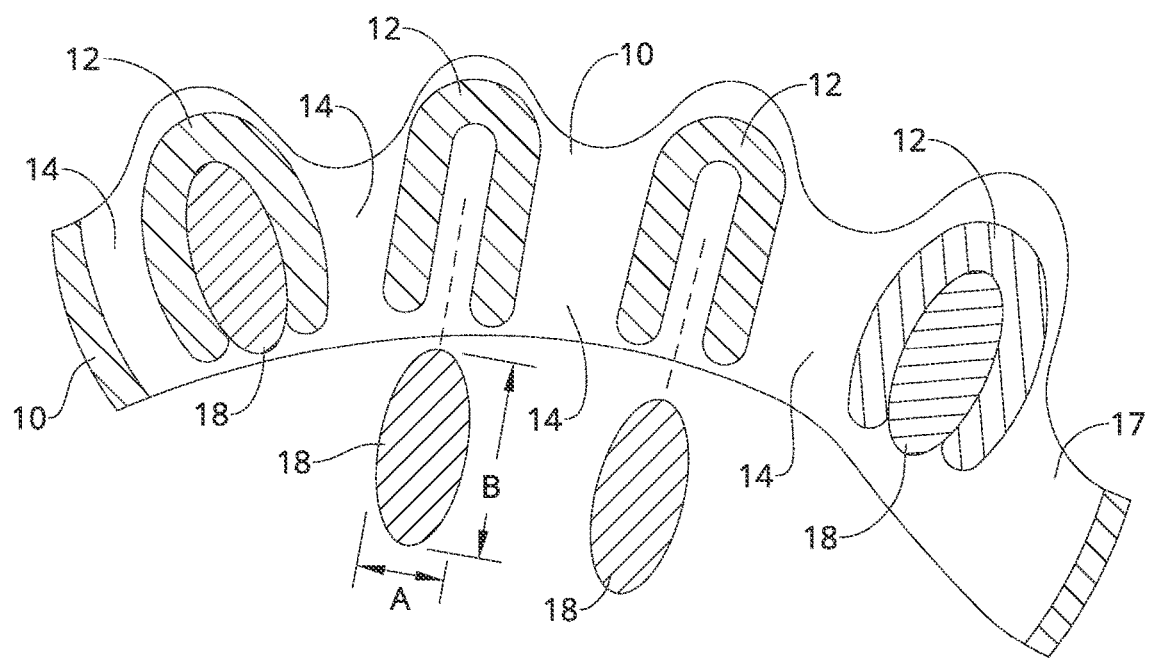
FIG. 8 is a section view of an exemplary embodiment of the present invention, taken along line 8-8 in FIG. 7, showing two of the four pills 18 removed while the other two pills 18 in the nested condition.
Figure 9:
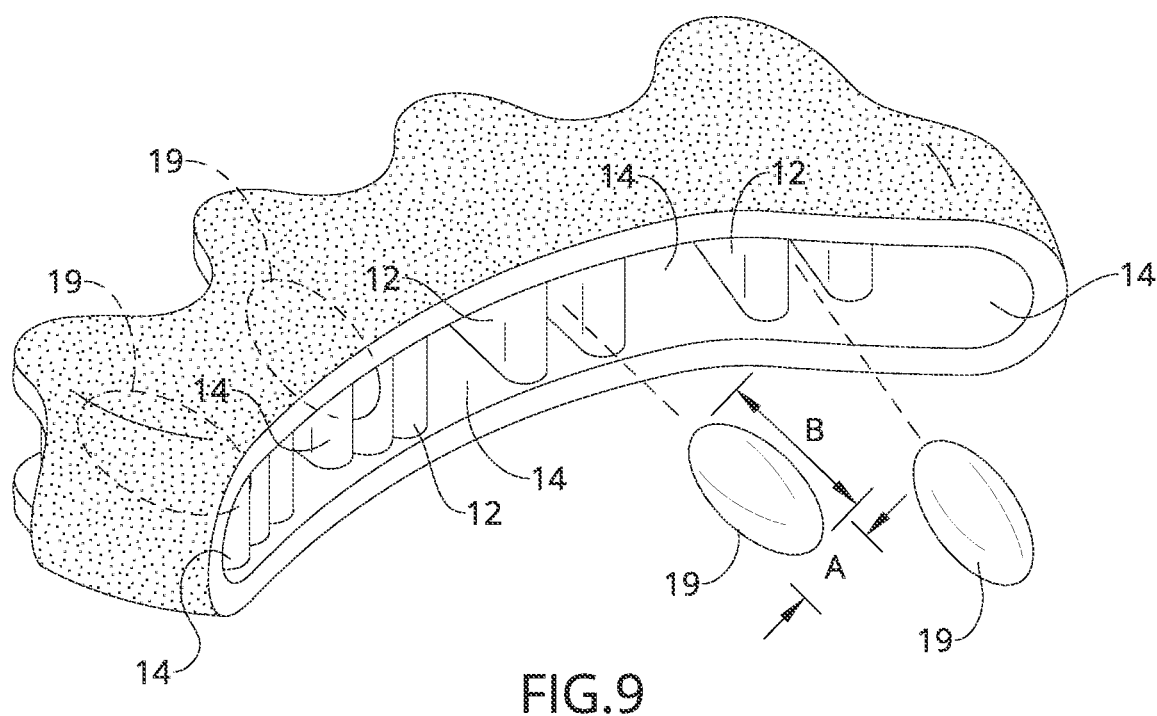
FIG. 9 is an exploded perspective view of an exemplary embodiment of the present invention, wherein the separator pills 19 are ellipsoids.

The present invention contemplates various separator pills 16, 18, 19, etc., are dimensioned and shaped to be nested into a toe wedge 12 (via its opening 13) to expand the width of the toe wedge 12 the pill is inserted into. In some embodiments, the distal end (the posterior end) of the pill 16, 18, 19 may protrude from the toe wedge 12. The separator pills 16, 18, 19, etc., are shaped and dimensioned so that the toe wedge 12 has a maximum width at an approximate (longitudinal) midportion or midsection as illustrated in FIGS. 4 and 8.

A first separator pill 16 may be fish-shaped, having a body portion 161 and a caudal fin portion 163. All or a portion of the caudal fin portion 163 may protrude from the toe wedge 12 during use. Thereby the fish shape/caudal fin portion 163 makes it easier to hold and insert into the wedge opening 13 while still being comfortable when pressed against the webbing of the toes. In embodiments, where the toe wedge 12 has openings 13 on both ends, then the fish shaped of the first separator pill 16 would also help prevent the first separator pill 16 from slipping through to the other side.

The first separator pill 16 may be hollow with a bracing element 165 extending laterally from sidewall to sidewall of the body portion 161. The dimensions of the first separator pill 16 may range from 0.5 inches to 2 inches for an anterior-end-to-posterior-end distance of the body portion 161 and range from 0.125 inches to 1 inch for a width of the body portion 161. The caudal fin portion 163 may be 0.25 inches to 1 inch wide.

A second separator pill 18 may have an oval plane section having principal diameters 'A' and 'B' ranging from 0.125 inches to 1 inch (diameter 'A') and 0.5 inches to 2 inches (diameter 'B'), respectively (while rectangular in cross section). The second separator pill 18 may be ellipsoid shaped having principal diameters 'A', 'B', and 'C' ranging from 0.125 inches to 1 inch, 0.5 inches 2 inches, and 0.125 inches to 1 inch, respectively. Note, in FIG. 9, 'C' is not shown, but it is assumed that diameter extends in a direction orthogonal to both 'A' and 'B'.

It is to be understood that the material of the pills 16, 18 may be made from various materials that facilitate the purpose of the present invention as disclosed herein. Likewise, the properties of the material have certain advantageous properties, such as a density that ranges from Shore 00 30 durometer to Shore A 90 durometer.

As a result, the present invention toe separator shell 10 and associated pills 16, 18, etc., embodies a method of restoring balance and healthy foot function through adjusting the density of the various pills 16, 18, 19, etc., wherein in certain embodiments, four pills 16, 18, 19, etc., may be utilized in a toe separator shell, wherein at least two or more of the four pills 16, 18, 19, etc. have different densities.

A method of using the present invention may include the following. The toe separator shell 10 disclosed herein may be provided. The user selects the type and density of the toe separator pills 16, 18, 19, etc. they want to use and insert them into the opening 11 of the toe separator wedges 12. The interior space of the toe separator wedge and the elastic properties of its walls help hold the toe separator pills 16, 18, 19, etc., in place within the wedge 12 in a nested condition, as illustrated in FIG. 1. The user positions the device onto the four middle toes (second, third and fourth toe) by pulling the toe separator shell pull tabs.

The user would selectively determine, based on comfort and individual needs, which density pills to use and which toe separator slots to insert the pills to separate the second, third and fourth toes adequately and comfortably. The user would pull on the toe separator shell pull tabs to snugly pull the device onto the toes more efficiently and with less risk of tearing the device.

A method of manufacturing the present invention may include the following. The invention could be injection molded and made from flexible materials including but not limited to silicone and rubber. It could also be molded from other materials such as foam.

The pull tabs are optional, all other elements such as the toe separator shell with slots and toe separator pills are necessary.

As used in this application, the term "about" or "approximately" refers to a range of values within plus or minus 10% of the specified number. And the term "substantially" refers to up to 80% or more of an entirety. Recitation of ranges of values herein are not intended to be limiting, referring instead individually to any and all values falling within the range, unless otherwise indicated, and each separate value within such a range is incorporated into the specification as if it were individually recited herein.

For purposes of this disclosure, the term "aligned" means parallel, substantially parallel, or forming an angle of less than 35.0 degrees. For purposes of this disclosure, the term "transverse" means perpendicular, substantially perpendicular, or forming an angle between 55.0 and 125.0 degrees. Also, for purposes of this disclosure, the term "length" means the longest dimension of an object. Also, for purposes of this disclosure, the term "width" means the dimension of an object from side to side. For the purposes of this disclosure, the term "above" generally means superjacent, substantially superjacent, or higher than another object although not directly overlying the object. Further, for purposes of this disclosure, the term "mechanical communication" generally refers to components being in direct physical contact with each other or being in indirect physical contact with each other where movement of one component affect the position of the other.

The use of any and all examples, or exemplary language ("e.g.," "such as," or the like) provided herein, is intended merely to better illuminate the embodiments and does not pose a limitation on the scope of the embodiments or the claims. No language in the specification should be construed as indicating any unclaimed element as essential to the practice of the disclosed embodiments.

In the following description, it is understood that terms such as "first," "second," "top," "bottom," "up," "down," and the like, are words of convenience and are not to be construed as limiting terms unless specifically stated to the contrary.

It should be understood, of course, that the foregoing relates to exemplary embodiments of the invention and that modifications may be made without departing from the spirit and scope of the invention as set forth in the claims.

What is claimed is:

1. A toe separator system comprising:
a toe separator shell comprising a leading edge configured to be adjacent a distal end of a user's toes, and a trailing edge configured to be adjacent a proximal end of the user's toes defining an area intended for adjacent placement of the toes, where a shell direction from the leading edge to the trailing edge defines a longitudinal direction of the toe separator shell;
the area having a plurality of toe wedges, wherein a space between each two adjacent toe wedges of the plurality of toe wedges defines a toe slot;
each toe wedge of the plurality of toe wedges defines a U-shape, wherein legs of the U-shape extend in the longitudinal direction so as to define a pill-receiving volume and an opening which faces the trailing edge of the toe separator shell that communicates an external environment with the pill-receiving volume; and
a plurality of separator pills dimensioned and shaped to be removably received in the pill-receiving volume via the opening so that a maximum width of the toe wedge is localized at a midportion of the toe wedge that extends in a direction perpendicular to the longitudinal direction between the adjacent toe slots.

2. The toe separator system of claim 1, wherein at least one of the plurality of separators pills has an oval plane section.

3. The toe separator system of claim 2, wherein no more than five percent of the oval plane section protrudes from the pill-receiving volume when received therein in a nested condition.

4. The toe separator system of claim 1, wherein at least one of the plurality of separator pills has a fish shape having a caudal fin portion.

5. The toe separator system of claim 4, wherein the caudal fin portion substantially protrudes from the opening in a nested condition.

6. The toe separator system of claim 1, wherein the plurality of separator pills have a plurality of densities, respectively.

7. A method of improving foot functionality, the method comprising:
providing the toe separator system of claim 6;
urging a separator pill into each pill-receiving volume, respectively;
sliding the toe separator shell over a set of toes of a patient; and
swapping out a separator pill of at least one pill-receiving volume based on feedback from the patient.

8. The toe separator system of claim 1, wherein each of the plurality of toe wedges has elastic properties for snugly accommodating one of the plurality of separator pills.

9. The toe separator system of claim 1, wherein each of the plurality of separator pills has an internal bracing element disposed at a maximum width of the separator pill so that the bracing element aligns with said maximum width of the toe wedge.

* * * * *